United States Patent
Breton et al.

(12)

(10) Patent No.: US 6,267,971 B1
(45) Date of Patent: Jul. 31, 2001

(54) USE OF CINNAMIC ACID OR OF ITS DERIVATIVES IN A COSMETIC FIRMING COMPOSITION

(75) Inventors: Lionel Breton, Versailles; Florence Girerd, Paris; Béatrice Renault, Saint Maurice, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/216,862

(22) Filed: Dec. 21, 1998

(30) Foreign Application Priority Data

Dec. 19, 1997 (FR) .................................................. 97 16180

(51) Int. Cl.$^7$ ................................. A61K 6/00; A61K 7/00
(52) U.S. Cl. .......................... 424/401; 514/969; 514/846
(58) Field of Search ........................... 424/401; 514/969, 514/846

(56) References Cited

U.S. PATENT DOCUMENTS

| 4,466,961 | 8/1984 | Szijjarto nee Auber et al. |
| 5,093,109 | 3/1992 | Mausner . |
| 5,536,500 | * 7/1996 | Galey et al. ........................ 424/401 |
| 5,837,697 | * 11/1998 | Blank et al. ........................ 514/159 |
| 5,952,373 | 9/1999 | Lanzendorfer et al. . |

FOREIGN PATENT DOCUMENTS

| 0 103 878 | 9/1983 | (EP) . |
| 0 451 889 A1 | 10/1991 | (EP) . |
| 0664290 | 7/1995 | (EP) . |
| 0716847 | 6/1996 | (EP) . |
| 0 925 779 A1 | 11/1998 | (EP) . |
| 1 269 573 | 7/1961 | (FR) . |
| 2 315 908 | 1/1977 | (FR) . |
| 57-167921 | 10/1982 | (JP) . |
| 63-277615 | 11/1988 | (JP) . |
| 64-13018 | 1/1989 | (JP) . |
| 5-78230 | 3/1993 | (JP) . |
| 5-105621 | 4/1993 | (JP) . |
| 5-105643 | 4/1993 | (JP) . |
| 5-221845 | 8/1993 | (JP) . |
| 5-310526 | 11/1993 | (JP) . |
| 6-321754 | 11/1994 | (JP) . |
| 7-300469 | 11/1995 | (JP) . |
| 8-12664 | 1/1996 | (JP) . |
| 8-259421 | 10/1996 | (JP) . |
| 9-124474 | 5/1997 | (JP) . |
| 9-132527 | 5/1997 | (JP) . |
| WO 92/07544 | 5/1992 | (WO) . |
| 99/32078 | 7/1999 | (WO) . |

OTHER PUBLICATIONS

English abstract of JP 5–221845.
English abstract of EP 0506961.
English abstract of JP 5–310526.
English abstract of JP 013018.
English abstract of JP 5–78230.
English abstract of JP 5–105621.
English abstract of JP 5–105643.
English abstract of JP 6–321754.
English abstract of JP 9–124474.
English abstract of JP 9–132527.
English abstract of EP 0 103 878.
Claims of 63–277615 (in French).
Database WPI, Week 8936, Derwent Publications Ltd., London, AN 89–258961.
W.A. Poucher: "Poucher's Perfumes . . . ", Cosmetics & Soaps, vol. 1.
P. Rovesti, "Recheches sur l'action . . . ", PARFUMERIE MOD., vol. 48, No. 54, 1956.
Database WPI, Week 8802, XP002081837, "Hair rinsing . . . ".
Patent Abstracts of Japan, vol. 017, No. 674, Dec. 10, 1993.
Patent Abstracts of Japan, vol. 018, No. 118, Feb. 25, 1994.

* cited by examiner

Primary Examiner—Thurman K. Page
Assistant Examiner—Todd D Ware
(74) Attorney, Agent, or Firm—Burns, Doane, Swecker & Mathis, L.L.P.

(57) ABSTRACT

The invention relates to the use of cinnamic acid, or of at least one of its derivatives, in a cosmetic composition as a firming agent for the skin and/or mucous membranes.

The invention also relates to a firming composition comprising cinnamic acid or at least one of its derivatives.

69 Claims, No Drawings

USE OF CINNAMIC ACID OR OF ITS DERIVATIVES IN A COSMETIC FIRMING COMPOSITION

The invention relates to the use of cinnamic acid, or of at least one of its derivatives, in a cosmetic firming composition. In particular, the compositions of the invention are intended to stimulate the restructuring of the skin and/or mucous membranes by stimulating the synthesis of collagen.

The invention also relates to a firming composition comprising cinnamic acid or at least one of its derivatives.

Human skin consists of two compartments, i.e. a superficial compartment, the epidermis, and a deep compartment, the dermis.

Natural human epidermis is composed mainly of three types of cells: the keratinocytes, which form the great majority, the melanocytes and the Langerhans cells. Each of these cell types contributes, by virtue of its intrinsic functions, towards the essential role played in the body by the skin.

The dermis gives the epidermis a solid support. It is also the epidermis, nourishing factor. It consists mainly of fibroblasts and of an extracellular matrix composed mainly of collagen, elastin and a substance known as ground substance, these components being synthesized by the fibroblasts. Leukocytes, mastocytes and tissue macrophages are also found therein. It is also composed of blood vessels and nerve fibres. In normal skin, i.e. skin which is not pathological or scarred, the fibroblasts are in the quiescent state, i.e. non-proliferative, of low metabolic activity and immobile.

The collagen fibres give the dermis solidity. They are very strong but are sensitive to certain enzymes known as collagenases. In the dermis, the collagen fibres consist of fibrils sealed together, thus forming more than ten different types of structures. The solidity of the dermis is mainly due to the overlapping of the collagen fibres packed against each other in all directions. The collagen fibres contribute towards the elasticity and tonicity of the skin and/or mucous membranes.

The collagen fibres are constantly renewed, but this renewal decreases with age, which leads to thinning of the dermis. However, this thinning of the dermis is also due to pathological causes such as, for example, the hypersecretion of corticoid hormones, certain diseases (Marfan's syndrome, Ehlers-Danlos syndrome) or vitamin deficiencies (scurvy). It is also accepted that extrinsic factors such as ultraviolet radiation, tobacco or certain treatments (retinoic acid and derivatives, glucocorticoids, vitamin D and derivatives, for example) also have an effect on the skin and on its level of collagen. Degradation of the collagen fibres results in the appearance of loose, wrinkled skin which people have always tried to combat, since skin which looks smooth and taut is preferred.

Moreover, during the menopause, the main changes relating to the dermis are a decrease in the level of collagen and in the thickness of the dermis. In menopausal women, this results in thinning of the skin and/or mucous membranes. Women thus experience a sensation of "dry skin" or of skin which feels tight and an increase in the level of surface wrinkles and fine lines is observed. The skin looks rough to the touch. Lastly, the skin is less supple.

It is demonstrated that women lose 2.1% of their level of collagen per year after the menopause and that 30% is lost in the first five years after the menopause.

The importance of the presence of collagen fibres in the skin and the importance of maintaining, or even reinforcing, their presence can thus be appreciated.

It is thus important to have available products whose effects are directed towards maintaining the level of collagen in the skin and maintaining the skin's smooth and taut appearance.

In this regard, the Applicant has discovered, surprisingly and unexpectedly, that cinnamic acid or its derivatives have the property of stimulating the synthesis of collagen.

Cinnamic acid is present in trans form in the essential oils of basil or of cinnamon, in Peruvian balsam and in cocoa leaves. The cis form is present in the oil from *Alpinia malacensis*.

In the prior art, cinnamic acid or its derivatives are known to be used in compositions for preventing bedsores (JP 07 242 558), as an anti-ultraviolet active agent (U.S. Pat. No. 5,093,109), in permanent-waving compositions (DE 3,301,515, DE 2,912,477 and EP 22,996), in hair lotions (JP 7,053,401 and JP 3,041,413), in depigmenting compositions (JP 5,221,845 and JP 1,186,811) and as antioxidant (EP 664,290).

To the Applicant's knowledge, the use of cinnamic acid or of its derivatives to stimulate the synthesis of collagen has never been described in the prior art.

The subject of the invention is thus the use, in a cosmetic composition, of an effective amount of cinnamic acid or of at least one of its derivatives, the composition being intended to stimulate the synthesis of collagen.

Thus, according to the invention, the cinnamic acid or its derivatives can be of natural or synthetic origin. The term natural origin refers to cinnamic acid, or its derivatives, prepared from plant material in which they are found in the natural state. The term synthetic origin refers to cinnamic acid, or its derivatives, prepared by chemical synthesis or by biotechnology.

Thus, in the text hereinbelow, the term cinnamic acid is understood to denote cinnamic acid, or its derivatives, of natural or synthetic origin, in purified form or any preparation containing them.

Among the cinnamic acid derivatives which can be used according to the invention, mention may be made, for example, of mono- and polyhydroxycinnamic acids, alcohols, aldehydes, esters and derivatives.

Cinnamic acid is preferably used according to the invention.

Needless to say, it is possible according to the invention to use cinnamic acid or its derivatives alone or as a mixture.

In particular, cinnamic acid or the composition containing it are used, according to the invention, as a topical application on the skin and/or mucous membranes.

It has been seen above that collagen is involved in the solidity of the dermis, thus in the firmness of the skin and/or mucous membranes.

Hence, one of the aspects of the invention is thus to propose the use, in a cosmetic composition, of an effective amount of cinnamic acid or of at least one of its derivatives, the cinnamic acid or the composition being intended to reduce the signs of ageing on the skin, more particularly to reduce the appearance of loose and/or wrinkled skin.

Another aspect of the invention is thus to propose the use, in a cosmetic composition, of an effective amount of cinnamic acid or of at least one of its derivatives, the cinnamic acid or the composition being intended to stimulate the firming of the skin and/or mucous membranes.

According to another aspect also, the subject of the invention is the use, in a cosmetic composition, of an effective amount of cinnamic acid or of at least one of its derivatives, the cinnamic acid or the composition being intended to promote smoothing of the skin and/or to tighten the skin.

According to yet another aspect, the subject of the invention is the use, in a cosmetic composition, of an effective amount of cinnamic acid or of at least one of its derivatives, the cinnamic acid or the composition being intended to combat the effects of the menopause on the skin, more particularly the effects of the menopause on collagen.

The amount of cinnamic acid which can be used according to the invention obviously depends on the desired effect and must be in an amount which is effective for stimulating the synthesis of collagen.

For example, the amount of cinnamic acid which can be used according to the invention can range, for example, from $10^{-6}\%$ to 10% and preferably from $10^{-3}\%$ to 5% of the total weight of the composition.

It is possible to use, in the compositions of the invention, the cinnamic acid in combination with another product which stimulates collagen synthesis. Among these other products which stimulate collagen synthesis, mention may be made of plant hormones or else vitamin C or its derivatives.

Among the plant hormones, mention may be made of auxins such as 3-indoleacetic acid (IAA), 4-chloro-3-indoleacetic acid (4-Cl-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde and indoleacetonitrile.

β-Naphthoxyacetic acid is preferably used according to the invention.

Since the skin is made up of many components other than collagen, it turns out to be advantageous, when synthesis of the skin is promoted with cinnamic acid, to simultaneously promote the synthesis of these other components such as, for example, lipids.

Thus, it is possible to use, in the compositions according to the invention, the cinnamic acid or one of its derivatives in combination with another product which, for example, stimulates lipid synthesis.

In this regard, plant hormones such as auxins, and particularly β-naphthoxyacetic acid can also be mentioned.

Thus, the subject of the invention is a cosmetic composition comprising cinnamic acid or one of its derivatives and at least one other product which stimulates lipid synthesis.

A subject of the invention is also a cosmetic firming composition comprising, in a cosmetically acceptable medium, an effective amount of cinnamic acid or of at least one of its derivatives.

A subject of the invention is also a cosmetic composition for making the skin smooth or taut, comprising, in a cosmetically acceptable medium, an effective amount of cinnamic acid or of at least one of its derivatives.

A subject of the invention is also a cosmetic composition for stimulating collagen synthesis, comprising, in a cosmetically acceptable medium, an effective amount of cinnamic acid or of at least one of its derivatives.

A subject of the invention is also a cosmetic composition for combating the effects of the menopause on the skin, comprising, in a cosmetically acceptable medium, an effective amount of cinnamic acid or of at least one of its derivatives.

Lastly, the subject of the invention is a cosmetic composition for combating the effects of the menopause on collagen, comprising, in a cosmetically acceptable medium, an effective amount of cinnamic acid or of at least one of its derivatives.

The term cosmetically acceptable medium refers to a medium which is compatible with the skin, mucous membranes, the nails and the hair.

In addition, a subject of the invention is compositions comprising, in addition to cinnamic acid or one of its derivatives, another compound having the property of stimulating collagen synthesis, such as, in particular, plant hormones (for example auxins) or vitamin C and its derivatives.

A subject of the invention is also compositions comprising, in addition to cinnamic acid or one of its derivatives, a compound having the property of stimulating lipid synthesis, particularly synthesis of the skin's total lipids.

Needless to say, the composition according to the invention comprises a cosmetically acceptable support and can be in any pharmaceutical form normally used for topical application, in particular in the form of an aqueous, aqueous-alcoholic or oily solution, an oil-in-water, water-in-oil or multiple emulsion, an aqueous or oily gel, a liquid, pasty or solid anhydrous product, a dispersion of oil in an aqueous phase using spherules, it being possible for these spherules to be polymer nanoparticles such as nanospheres and nanocapsules or, better still, lipid vesicles of ionic and/or nonionic type.

This composition can be more or less fluid and can have the appearance of a white or coloured cream, an ointment, a milk, a lotion, a serum, a paste or a mousse. It can optionally be applied to the skin in the form of an aerosol. It can also be in solid form and, for example, in the form of a stick. It can be used as a care product, as a cleansing product, as a make-up product or as a simple deodorant product.

In a known manner, the composition according to the invention can also contain adjuvants which are common in the cosmetic and dermatological fields, such as hydrophilic or lipophilic gelling agents, hydrophilic or lipophilic active agents, preserving agents, antioxidants, solvents, fragrances, fillers, screening agents, pigments, chelating agents, odour absorbers and dyestuffs. The amounts of these various adjuvants are those used conventionally in the fields considered, and, for example, from 0.01% to 20% of the total weight of the composition. Depending on their nature, these adjuvants can be introduced into the fatty phase, into the aqueous phase, into the lipid vesicles and/or into the nanoparticles.

When the composition of the invention is an emulsion, the proportion of the fatty phase can range from 5% to 80% by weight, and preferably from 5% to 50%, of the total weight of the composition. The oils, the emulsifiers and the co-emulsifiers used in the composition in emulsion form are chosen from those used conventionally in the field considered. The emulsifier and the co-emulsifier are present in the composition in a proportion ranging from 0.3% to 30% by weight, and preferably from 0.5% to 20%, of the total weight of the composition.

As oils which can be used in the invention, mention may be made of mineral oils, oils of plant origin (apricot oil, sunflower oil), oils of animal origin, synthetic oils, silicone oils and fluoro oils (perfluoropolyethers). Fatty alcohols (cetyl alcohol), fatty acids and waxes (beeswax) can also be used as fatty substances.

As emulsifiers and co-emulsifiers which can be used in the invention, mention may be made, for example, of fatty acid esters of polyethylene glycol, such as PEG-40 stearate and PEG-100 stearate, and fatty acid esters of polyols, such as glyceryl stearate and sorbitan tristearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

The composition can contain other hydrophilic active agents such as proteins or protein hydrolysates, amino acids, polyols, urea, allantoin, sugars and sugar derivatives, water-soluble vitamins, plant extracts and hydroxy acids.

Retinol (vitamin A) and its derivatives, tocopherol (vitamin E) and its derivatives, essential fatty acids, ceramides, essential oils and salicylic acid and its derivatives can be used as lipophilic active agents.

It is also possible according to the invention to use, in combination with the cinnamic acid or at least one of its derivatives, compounds chosen from

- plant hormones;
- antibacterial agents such as macrolides, pyranosides and tetracyclines, and in particular erythromycin;
- calcium antagonists such as verapamil and diltiazem;
- OH radical scavengers such as dimethyl sulphoxide;
- plant extracts such as those from Iridaceae or from soybean, these extracts also possibly containing isoflavones;
- extracts from microorganisms including, in particular, bacterial extracts such as those from non-photosynthetic filamentous bacteria.

Other compounds can also be added to the above list, namely, for example, potassium-channel openers such as diazoxide and minoxidil, spiroxazone, phospholipids such as lecithin, linoleic and linolenic acids, salicylic acid and its derivatives described in French patent FR 2,581,542, such as salicylic acid derivatives bearing an alkyl group containing from 2 to 12 carbon atoms in position 5 of the benzene ring, hydroxycarboxylic or ketocarboxylic acids and their esters, lactones and their corresponding salts, anthralin, carotenoids, eicosatetraenoic and eicosatrienoic acids or their esters and amides, and vitamin D and its derivatives.

According to the invention, it is possible, inter alia, to combine cinnamic acid with other active agents intended in particular for preventing and/or treating skin complaints. Among these active agents, mention may be made, for example of:

- agents which modify skin differentiation and/or proliferation and/or pigmentation, such as retinoic acid and its isomers, retinol and its esters, vitamin D and its derivatives, oestrogens such as oestradiol, kojic acid or hydroquinone;
- agents which modify the adhesion of bacteria to the skin and/or to mucous membranes, such as honey, in particular acacia honey and certain sugar derivatives;
- antiparasitic agents, in particular metronidazole, crotamiton or pyrethroids;
- antifungal agents, in particular compounds belonging to the imidazole class such as econazole, ketoconazole or miconazole or their salts, polyene compounds such as amphotericin B, compounds of the allylamine family such as terbinafine, or octopirox;
- antiviral agents such as acyclovir;
- steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;
- anaesthetics such as lidocaine hydrochloride and its derivatives;
- anti-pruriginous agents such as thenaldine, trimeprazine or cyproheptadine;
- keratolytic agents such as α- and β-hydroxycarboxylic or β-ketocarboxylic acids, their salts, amides or esters, and more particularly hydroxy acids such as glycolic acid, lactic acid, salicylic acid, citric acid and fruit acids in general, and 5-n-octanoylsalicylic acid;
- anti-free-radical agents such as α-tocopherol or its esters, superoxide dimutases, certain metal-chelating agents or ascorbic acid and its esters;
- anti-seborrhoeic agents such as progesterone;
- antidandruff agents such as octopirox or zinc pyrithione;
- anti-acne agents such as retinoic acid or benzoyl peroxide;
- substances such as antagonists of substance P, of CGRP or of bradykinin or NO synthase inhibitors, compounds described as being active in the treatment of sensitive skin and as having anti-irritant effects, in particular with respect to irritant compounds which may be present in the compositions.

Thus, another subject of the invention relates to a composition comprising an effective amount of cinnamic acid or of one of its derivatives and at least one agent chosen from antibacterial agents, antiparasitic agents, antifungal agents, antiviral agents, anti-inflammatories, anti-pruriginous agents, anaesthetics, keratolytic agents, anti-free-radical agents, anti-seborrhoeic agents, antidandruff agents, anti-acne agents, agents for modifying skin differentiation and/or proliferation and/or pigmentation, antagonists of substance P, of CGRP or of bradykinin, or NO synthase inhibitors.

Moisturizers such as polyols (for example glycerol), vitamins (for example D-panthenol), anti-inflammatory agents, calmatives (allantoin, cornflower water), UVA and UVB screening agents, matt-effect agents (for example the partially crosslinked polydimethylorganosiloxanes sold under the name KSG® by Shin Etsu), and mixtures thereof can be used in particular as active agents.

Anti-wrinkle active agents, and in particular tensioning products such as plant proteins and their hydrolysates, in particular the soybean protein extract sold under the name Eleseryl® by the company LSN or the oat derivative sold under the name Reductine® by the company Silab, can also be added.

Needless to say, the cinnamic acid or its derivatives can be used in the preparation of cosmetic and/or pharmaceutical compositions, particularly dermatological compositions, intended to stimulate collagen synthesis.

Other characteristics and advantages of the invention will emerge more clearly from the examples which follow, which are given as non-limiting illustrations. In the text hereinbelow and hereinabove the proportions are given as a percentage by weight, except where otherwise indicated.

EXAMPLE 1

Study of the effect of cinnamic acid on collagen synthesis.

The study is carried out by measuring the incorporation of radioactive proline into normal human dermal fibroblast cultures.

The fibroblast cultures are prepared according to the standard methods of cell culturing, i.e. in MEM/M199 medium sold by the company Gibco, in the presence of sodium bicarbonate (1.87 mg/ml), L-glutamine (2 mM), penicillin (50 IU/ml) and 10% foetal calf serum (Gibco).

The test is carried out on cell cultures at 80% confluence on 24-well plates. Cinnamic acid, at a concentration of $10^{-4}$M is placed in contact with the cells for 48 hours. Labelling with tritiated proline (L-[2,3-$^3$H]-proline sold by Amersham, 33 $\mu$Ci/ml) is carried out for 24 hours. The level of tritiated proline incorporated is measured at the end of the test by acidic precipitation of the proteins on filters and counting by liquid scintillation.

The results are assessed relative to a control consisting of cells which have not been treated with cinnamic acid.

A positive control (20 μg/ml of vitamin C), which is known to stimulate collagen synthesis, and a negative control ($10^{-6}$M retinoic acid), which is known to inhibit collagen synthesis, are introduced into the test by way of reference.

The results of this test are given in the following table.

| Treatment | cpm | % | p |
|---|---|---|---|
| Untreated cells | 19261 | 100 | — |
| Cinnamic acid | 26209 | 136 | <0.01 |
| Retinoic acid | 13160 | 68 | <0.01 |
| Vitamin C | 40344 | 209 | <0.01 | cpm: counts per minute
p: confidence interval calculated according to the Dunett method.

These results show that cinnamic acid significantly stimulates the incorporation of proline into collagen and that it thus has an effect on collagen neosynthesis.

EXAMPLE 2

Examples of compositions according to the invention. These compositions are obtained by the usual techniques commonly used in cosmetics or pharmacy.

| Composition 1: Care cream | |
|---|---|
| Beeswax | 1.5% |
| Apricot kernel oil | 13.0% |
| Preserving agents | 0.3% |
| Fragrance | 0.4% |
| β-Naphthoxyacetic acid | 0.01% |
| Cinnamic acid | 0.01% |
| Xanthan | 0.5% |
| Cyclopentadimethylsiloxane | 5.0% |
| Sterilized demineralized water | 69.28% |
| Sucrose mono-di-palmitostearate | 3.0% |
| Methylglucose sesquistearate | 3.0% |
| Stearic acid | 1.0% |
| Cetyl alcohol | 3.0% |

| Composition 2: Body oil | |
|---|---|
| Liquid petroleum jelly | 47.98% |
| Apricot kernel oil | 6.0% |
| Fragrance | 1.0% |
| β-Naphthoxyacetic acid | 0.01% |
| Cinnamic acid | 0.01% |
| Cyclopentadimethylsiloxane | 45.0% |

| Composition 3: Make-up-removing milk | |
|---|---|
| 2-Ethylhexyl palmitate | 10.5% |
| Liquid fraction of karite butter | 16.5% |
| Preserving agents | 0.3% |
| Fragrance | 0.15% |

| Composition 3: Make-up-removing milk (-continued) | |
|---|---|
| β-Naphthoxyacetic acid | 0.01% |
| Cinnamic acid | 0.01% |
| Sodium hydroxide | 0.04% |
| Carboxyvinyl polymer | 0.2% |
| Sterilized demineralized water | 69.79% |
| Mixture of cetylstearylglucoside and of cetyl and stearyl alcohols | 2.5% |

| Composition 4: Care cream | |
|---|---|
| Beeswax | 1.5% |
| Apricot kernel oil | 13.0% |
| Preserving agents | 0.3% |
| Fragrance | 0.4% |
| β-Naphthoxyacetic acid | 0.01% |
| Cinnamic acid | 0.01% |
| Ethyl cinnamate | 0.01% |
| Xanthan | 0.5% |
| Cyclopentadimethylsiloxane | 5.0% |
| Sterilized demineralized water | 69.27% |
| Sucrose mono-di-palmitostearate | 3.0% |
| Methylglucose sesquistearate | 3.0% |
| Stearic acid | 1.0% |
| Cetyl alcohol | 3.0% |

What is claimed is:

1. A method for reducing the signs of aging of the skin by stimulating collagen synthesis comprising applying a cosmetic composition comprising an amount of cinnamic acid or a derivative thereof effective to reduce the signs of skin aging.

2. A method for stimulating firming of the skin and/or mucous membranes by stimulating collagen synthesis comprising applying a cosmetic composition comprising an effective amount of cinnamic acid or a derivative thereof for stimulating the firming of the skin and/or mucous membranes.

3. A method for promoting smoothing of the skin and/or tightening of the skin by stimulating collagen synthesis comprising applying a cosmetic composition comprising an amount of cinnamic acid or a derivative thereof effective to promote smoothing of the skin and/or tightening of the skin.

4. A method for stimulating collagen synthesis comprising applying a cosmetic composition comprising an amount of cinnamic acid or a derivative thereof effective for stimulating collagen synthesis.

5. A method for alleviating the effects of menopause on collagen by stimulating collagen synthesis comprising applying a cosmetic composition comprising an amount of cinnamic acid or a derivative thereof effective for alleviating the effects of menopause on collagen.

6. The method of claim 1, wherein said cosmetic composition is topically applied to the skin and/or mucous membranes.

7. The method of claim 2, wherein said composition is topically applied to the skin and/or mucous membranes.

8. The method of claim 3, wherein said composition is topically applied to the skin and/or mucous membranes.

9. The method of claim 4, wherein said composition is topically applied to the skin and/or mucous membranes.

10. The method of claim 5, wherein said composition is topically applied to the skin and/or mucous membranes.

11. The method of claim 1, wherein said cinnamic acid derivative is selected from the group consisting of mono and polyhydroxy cinnamic acids, alcohols, aldehydes, esters and derivatives thereof.

12. The method of claim 2, wherein said cinnamic acid derivatives are selected from the group consisting of mono and polyhydroxy cinnamic acids, alcohols, aldehydes, esters and derivatives thereof.

13. The method of claim 3, wherein said cinnamic acid derivatives are selected from the group consisting of mono and polyhydroxy cinnamic acids, alcohols, aldehydes, esters and derivatives thereof.

14. The method of claim 4, wherein said cinnamic acid derivatives are selected from the group consisting of mono and polyhydroxy cinnamic acids, alcohols, aldehydes, esters and derivatives thereof.

15. The method of claim 5, wherein said cinnamic acid derivatives are selected from the group consisting of mono and polyhydroxy cinnamic acids, alcohols, aldehydes, esters and derivatives thereof.

16. The method of claim 1, wherein the amount of said cinnamic acid or derivative thereof ranges from $10^{-6}\%$ to 10 relative to the total weight of the composition.

17. The method of claim 2, wherein the amount of said cinnamic acid or derivative thereof ranges from $10^{-6}\%$ to 10% relative to the total weight of the composition.

18. The method of claim 3, wherein the amount of said cinnamic acid or derivative thereof ranges from $10^{-6}\%$ to 10% relative to the total weight of the composition.

19. The method of claim 4, wherein the amount of said cinnamic acid or derivative thereof ranges from $10^{-6}\%$ to 10% relative to the total weight of the composition.

20. The method of claim 5, wherein the amount of said cinnamic acid or derivative thereof ranges from $10^{-6}\%$ to 10% relative to the total weight of the composition.

21. The method of claim 1, wherein the amount of said cinnamic acid or derivative thereof ranges from $10^{-3}\%$ to 5% relative to the total weight of the composition.

22. The method of claim 2, wherein the amount of said cinnamic acid or derivative thereof ranges from $10^{-3}\%$ to 5% relative to the total weight of the composition.

23. The method of claim 3, wherein the amount of said cinnamic acid or derivative thereof ranges from $10^{-3}\%$ to 5% relative to the total weight of the composition.

24. The method of claim 4, wherein the amount of said cinnamic acid or derivative thereof ranges from $10^{-3}\%$ to 5% relative to the total weight of the composition.

25. The method of claim 5, wherein the amount of said cinnamic acid or derivative thereof ranges from $10^{-3}\%$ to 5% relative to the total weight of the composition.

26. The method of claim 1, which further comprises administration of another product which stimulates collagen synthesis.

27. The method of claim 2, which further comprises administration of another product which stimulates collagen synthesis.

28. The method of claim 3, which further comprises administration of another product which stimulates collagen synthesis.

29. The method of claim 4, which further comprises administration of another product which stimulates collagen synthesis.

30. The method of claim 5, which further comprises administration of another product which stimulates collagen synthesis.

31. The method of claim 26, wherein said other product is selected from the group consisting of plant hormones, vitamin C and derivatives thereof.

32. The method of claim 27, wherein said other product which stimulates collagen synthesis is selected from the group consisting of plant hormones, vitamin C and derivatives thereof.

33. The method of claim 28, wherein said other product which stimulates collagen synthesis is selected from the group consisting of plant hormones, vitamin C and derivatives thereof.

34. The method of claim 29, wherein said other product which stimulates collagen synthesis is selected from the group consisting of plant hormones, vitamin C and derivatives thereof.

35. The method of claim 5, wherein said other product which stimulates collagen synthesis is selected from the group consisting of plant hormones, vitamin C and derivatives thereof.

36. The method of claim 31, wherein said plant hormone is an auxin.

37. The method of claim 32, wherein said plant hormone is an auxin.

38. The method of claim 33, wherein said plant hormone is an auxin.

39. The method of claim 34, wherein said plant hormone is an auxin.

40. The method of claim 35, wherein said plant hormone is an auxin.

41. The method of claim 36, wherein said auxin is selected from the group consisting of 3-indoleacetic acid (IAA), 4-chloro-3-indoleacetic acid (4-C1-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde, and indoleacetonitrile.

42. The method of claim 37, wherein said auxin is selected from the group consisting of 3-indoleacetic acid (IAA), 4-chloro-3-indoleacetic acid (4-C1-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde, and indoleacetonitrile.

43. The method of claim 38, wherein said auxin is selected from the group consisting of 3-indoleacetic acid (IAA), 4-chloro-3-indoleacetic acid (4-C1-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde, and indoleacetonitrile.

44. The method of claim 39, wherein said auxin is selected from the group consisting of 3-indoleacetic acid (IAA), 4-chloro-3-indoleacetic acid (4-C1-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde, and indoleacetonitrile.

45. The method of claim 40, wherein said auxin is selected from the group consisting of the compounds that are recited in original claim 13.

46. The method according to claim 41, wherein said auxin is β-naphthoxyacetic acid.

47. The method according to claim 42, wherein said auxin is β-naphthoxyacetic acid.

48. The method of claim 43, wherein said auxin is β-naphthoxyacetic acid.

49. The method of claim 44, wherein said auxin is β-naphthoxyacetic acid.

50. The method of claim 45, wherein said auxin is β-naphthoxyacetic acid.

51. The method of claim 1, wherein said cinnamic acid or derivative thereof is administered with another product which stimulates lipid synthesis.

52. The method of claim 2, wherein said cinnamic acid or derivative thereof is administered with another product which stimulates lipid synthesis.

53. The method of claim 3, wherein said cinnamic acid or derivative thereof is administered with another product which stimulates lipid synthesis.

54. The method of claim 4, wherein said cinnamic acid or derivative thereof is combined with another product which stimulates lipid synthesis.

55. The method of claim 5, wherein said cinnamic acid or derivative thereof is administered with another product which stimulates lipid synthesis.

56. The method of claim 51, wherein said product which stimulates lipid synthesis is a plant hormone.

57. The method of claim 52, wherein said other product which stimulates lipid synthesis is a plant hormone.

58. The method of claim 53, wherein said other product which stimulates lipid synthesis is a plant hormone.

59. The method of claim 54, wherein said other product which stimulates lipid synthesis is a plant hormone.

60. The method of claim 55, wherein said other product which stimulates lipid synthesis is a plant hormone.

61. The method of claim 1, which further comprises administration of another product which stimulates collagen and/or lipid synthesis which is administered in an amount ranging from between $10^{-6}$% to 10% relative to the total weight of the composition.

62. The method of claim 2, which further comprises the administration of another product which stimulates collagen and/or lipid synthesis which is administered in an amount ranging from between $10^{-6}$% to 10% relative to the total weight of the composition.

63. The method of claim 3, which fuirther comprises the administration of another product which stimulates collagen and/or lipid synthesis which is comprised in an amount ranging from between $10^{-6}$% to 10% relative to the total weight of the composition which comprises said other product.

64. The method of claim 4, which further comprises the administration of another product which stimulates collagen and/or lipid synthesis which is comprised in an amount ranging from $10^{-6}$% to 10% relative to the total weight of the composition comprising said other product.

65. The method of claim 61, wherein the amount of said other product ranges from $10^{-3}$% to 10% relative to the total weight of the composition.

66. The method of claim 62, wherein the amount of said other product ranges from $10^{-3}$% to 5% relative to the total weight of the composition.

67. The method of claim 63, wherein the amount of said other product ranges from $10^{-3}$% to 5% relative to the total weight of the composition containing said other product.

68. The method of claim 64, wherein the amount of said other product ranges from $10^{-3}$% to 5% relative to the total weight of the composition containing said other product.

69. The method of claim 65, wherein the amount of said other product ranges from $10^{-3}$% to 5% relative to the total weight of the composition containing said other product.

* * * * *